United States Patent [19]

Yarita et al.

[11] Patent Number: 5,070,208

[45] Date of Patent: Dec. 3, 1991

[54] METHOD FOR CRYSTALLIZATION OF OPTICALLY ACTIVE TRYPTOPHAN

[75] Inventors: Kenichi Yarita; Takahisa Tada; Ryuichiro Kasatani, all of Kawasaki, Japan

[73] Assignee: Ajinomoto Company, Inc., Tokyo, Japan

[21] Appl. No.: 670,182

[22] Filed: Mar. 15, 1991

[30] Foreign Application Priority Data

Mar. 15, 1990 [JP] Japan ................................ 2-65270

[51] Int. Cl.$^5$ .......................................... C07D 209/20
[52] U.S. Cl. .................................................. 548/494
[58] Field of Search ........................................ 548/497

[56] References Cited

U.S. PATENT DOCUMENTS 3,450,712  6/1969  Hirotoshi et al. ................... 548/497

FOREIGN PATENT DOCUMENTS 789025  7/1968  Canada ................................ 548/497

Primary Examiner—David B. Springer
Attorney, Agent, or Firm—Oblon, Spivak, McClelland, Maier & Neustadt

[57] ABSTRACT

Optically active tryptophan is crystallized by a modification of a method of crystrallization of optically active tryptophan through neutralization by mixing an acidic or alkaline aqueous solution of optically active tryptophan, which is obtained by the removal of impurities from an acidic or alkaline aqueous solution of optically active tryptophan containing impurities which inhibit flocculation and crystallization of optically active tryptophan, with an alkali or an acid, by combining portions of an alkali or acid with portions of an acidic or alkaline aqueous solution of optically active tryptophan, from which the impurities have been removed, thereby neutralizing the aqueous solution containing optically active tryptophan such that the pH of the solution to be crystallized is kept in a range of 3 to 8, and simultaneously crystallizing optically active tryptophan as flocculated crystals.

8 Claims, 1 Drawing Sheet

METHOD FOR CRYSTALLIZATION OF OPTICALLY ACTIVE TRYPTOPHAN

BACKGROUND OF THE INVENTION

1. Field of the Invention

The present invention relates to a method for crystallizing optically active tryptophan.

2. Discussion of the Background

In the crystallization of L-tryptophan (hereafter simply referred to as L-Trp), it is known that pigments and other materials can be removed from the crystallization medium to crystallize tryptophan in good selectivity. L-Trp is isolated by adding an organic solvent such as isopropyl alcohol, or the like to an aqueous solution of L-Trp (Japanese Patent Application Laid-Open Nos. 59-39875 (scaly crystals), 60-30694 (scaly crystals), 61-12607 (scaly crystals), 63-177796 (scaly crystals)). In these cases, it is necessary to recover the organic solvent so that these processes are not advantageous from an economic viewpoint.

On the other hand, where L-Trp is crystallized from an aqueous solution by concentration without using an organic solvent, the precipitated crystals obtained are generally fine scaly crystals. Upon isolation using a centrifuge, these crystals form layers which result in poor separation of the mother liquor and a long period of time is required for isolation of the Trp crystals. The thus obtained crystals are dried only with difficulty which means a long period of time is also required for drying. In addition, when crystallization occurs through concentration, vigorous foaming sometimes makes concentration impossible (Japanese Patent Application Laid-Open No. 60-237054 (scaly crystals)). One method of improving crystallization has been reported in which a water-soluble cellulose derivative, a water-soluble polyvinyl compound or the like is added to an aqueous solution of L-Trp. At the same time, foaming is prevented and crystallization is effected by concentration (Japanese Patent Application Laid-Open No. 60-237054 (spherical crystals)). However, when a defoaming agent or a crystallization catalyst is added, there is a danger that these compounds might be brought into the final product.

As an alternative to crystallization by concentration, crystallization can be advantageously achieved through neutralization by adding an alkali or an acid to an acidic or aqueous alkaline solution of L-Trp. One known embodiment of the method involves adding an alkali or a acid to the total amount of an acidic or alkaline aqueous solution of L-Trp until its pH becomes neutral and mixing the solution by stirring. In this case, scaly microcrystals are generally precipitated which means that solid-liquid separation and drying of the product are unsatisfactory.

As stated above, it is difficult to crystallize and isolate L-Trp from an aqueous solution containing impurities. In most cases, impurities such as pigments, and the like are generally removed by using a synthetic resin or the like as an adsorbent prior to crystallization. One example to this method involves treating the aqueous solution with a weakly basic anionic exchange resin or an amphoteric ion exchange resin and then performing crystallization by concentration. (Japanese Patent Application Laid-Open No. 1-112991 (scaly crystals)). Even with this method, when crystallizing L-Trp, foaming is noted upon concentration, although the foaming is less vigorous because of the effect achieved by the treatment of the medium with resin to remove impurities. It is thus difficult to concentrate a slurry for crystallization of large quantities of L-Trp, without adding a defoaming agent to the system.

On the other hand, crystallization techniques other than crystallization by the addition of an organic solvent and crystallization by concentration are known, one of which is a method of forming layered flocculated crystals in which good solid-liquid separation is realized. The method comprises gradually adding a saturated solution of L-Trp at a high temperature to a slurry of L-Trp at a low temperature (Japanese Patent Application Laid-Open No. 62-265254). However, the dependency of L-Trp solubility on temperature is not as significant as for other amino acids (solubility of L-Trp in 100 g of water is 0.82 g at 0° C., 1.14 g at 25° C., 18 g at 40° C., 2.4 g at 60° C. and 3.4 g at 80° C.). Where crystallization upon cooling is performed, the rate of crystallization decreases. In order to enhance the rate of crystallization, it is necessary to elevate the temperature of the saturated L-Trp solution to about 80° C. In this case, however, a problem is encountered which is that decomposition of L-Trp is accelerated. A need therefore continues to exist for an improved method of crystallizing optically active tryptophan.

SUMMARY OF THE INVENTION

One object of the present invention is to provide a method for precipitating optically active tryptophan crystals from solution, which is characterized by good solid-liquid separation, by neutralization of a solution and using a centrifuge, without adding any defoaming agent or a crystallization catalyst to the solution or without heating the solution to a high temperature.

Briefly, this object and other objects of the present invention as hereinafter will become more readily apparent can be attained by a modification of the method of crystallization of optically active tryptophan through neutralization by mixing an acidic or alkaline aqueous solution of optically active tryptophan, which is obtained by the removal of impurities from an acidic or alkaline aqueous solution of optically active tryptophan containing impurities which inhibit flocculation and crystallization of optically active tryptophan, with an alkali or an acid, which comprises combining portions of an alkali or acid with portions of an acidic or alkaline aqueous solution of optically active tryptophan, from which the impurities have been removed, thereby neutralizing the aqueous solution containing optically active tryptophan such that the pH of the solution in which crystallization is occurring is kept in a range of 3 to 8, and simultaneously crystallizing optically active tryptophan as flocculated crystals.

DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
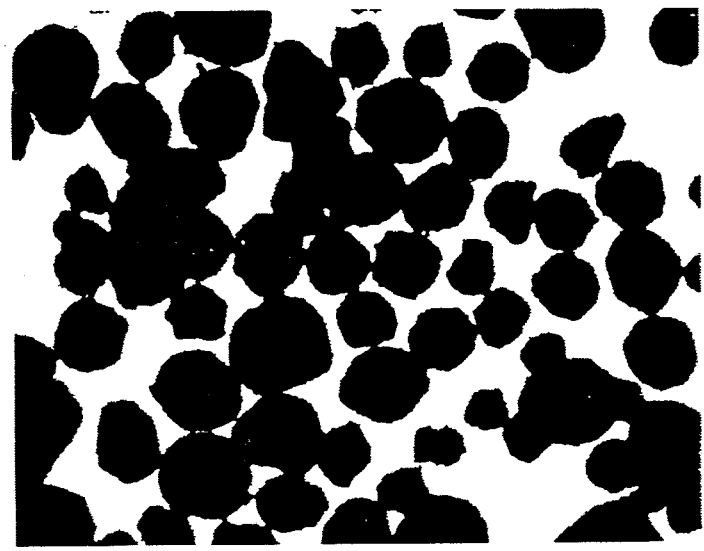
FIG. 1 is a microphotograph (40×) of the flocculated crystals of L-Trp prepared by the process of Example 1(a)

The tryptophan which is used as a starting material in the present invention may be prepared by any fermentation or synthetic process.

In fermentation processes, it is well known to prepare L-Trp using L-Trp-producing bacteria. Generally, many impurities are present in the fermentation broth obtained, in addition to L-Trp, and these impurities include those that inhibit flocculation and crystallization of L-Trp. Upon crystallization and isolation of L-Trp from the fermentation broth, cells are usually removed by filtration through a membrane, by sedimentation, or the like. However, such impurities remain in the thus obtained cell-free solution as they are. An example of an aqueous solution of optically active tryptophan containing impurities which inhibit flocculation and crystallization of optically active tryptophan referred to in the present invention include the cell-free solutions described above, and the like.

After adjusting the pH of the cell-free solution of L-Trp to an acidic pH of 1 to 3 or an alkaline pH of 10 to 14, the solution is concentrated and is neutralized by a known method to achieve crystallization of the L-Trp This method results in L-Trp crystals which are scaly micro-crystals. Even if the above concentrate obtained is subjected to neutralization and crystallization by the technique of the present invention (later described), the resulting L-Trp crystals are scaly micro-crystals which are different from the L-Trp flocculated crystals of the present invention, where the present method also achieves good solid-liquid separation when centrifuged.

It has now been found that, upon neutralization and crystallization of the acidic or alkaline aqueous solution obtained by removing impurities such as pigments, and the like from such an L-Trp solution, when the neutralization and crystallization (later described) are performed under the conditions of the present invention, flocculated crystals of L-Trp which exhibit good solid-liquid separation can be obtained for the first time. Crystals of L-Trp obtained by neutralization and crystallization steps which do not adopt the conditions of the present invention for neutralization and crystallization are scaly micro-crystals.

The impurities in a Trp solution such as pigments, and the like can be removed from the cell-free solution of L-Trp fermentation broth using, for example, adsorbent resin. Suitable adsorbent resins, include nonionic porous resins, such as DIAION SP207 manufactured by Mitsubishi Chemical Industry Co., Ltd., and amphoteric ion exchange resins, such as decoloring resin KS type and HS type manufactured by Hokuetsu Carbon Industry Co., Ltd. are appropriately used.

When an acidic or alkaline aqueous solution of optically active tryptophan containing the impurities which inhibit flocculation and crystallization of optically active tryptophan is subjected to the neutralization and crystallization treatment after the aqueous solution flows through the adsorbent resin to adsorb and remove the impurities such as pigments, and the like, under the conditions of the present invention, this growth of L-Trp crystals can be improved and L-Trp is precipitated as crystals which exhibit good solid-liquid separation. The treatment with adsorbent resin is generally performed in an acidic regime preferably at pH of 2 to 5, where the impurities such as pigments, and the like are removed with good selectivity. That is, for example, the cell-free solution of an L-Trp fermentation broth flows through the adsorbent resin, if necessary and desired, after its pH is adjusted to within the range of 2 to 5. If the L-Trp solution containing less amounts of impurities such as pigments, and the like is used, the treatment with adsorbent resin is unnecessary, needless to say. A temperature of the broth when it flows is between 5 and 50° C. and the flow rate is SV = 0.5 to 4, preferably SV (space velocity) = 1 to 2.

By mixing with an alkali or an acid the thus obtained acidic or alkaline aqueous solution of optically active tryptophan, from which the impurities which inhibit flocculation and crystallization of optically active tryptophan have been removed, optically active tryptophan can be crystallized upon neutralization.

Turning to the alkali and acid used herein, both are preferably inorganic from an economic viewpoint. Examples of alkalis include aqueous solutions of sodium hydroxide, ammonia, and the like. Examples of the acids include sulfuric acid, hydrochloric acid, and the like. The concentration of the alkali and the acid is not particularly limited.

Turning to the conditions for neutralization and crystallization, it has been found that by varying the conditions for neutralization and crystallization, the flocculated crystals precipitate and the crystals which exhibit good solid-liquid separation when using a centrifuge are obtained.

Investigations on the conditions for neutralization and crystallization reveal the following: The acidic (or alkaline) aqueous solution of L-Trp is mixed with the alkali (or acid) so as to maintain pH of the solution from which the L-Trp is to be crystallized (slurry to be crystallized) in a range of 3 to 8. Preferably, the mixing is performed so as to maintain the pH within this pH range. In view of yield (rate of crystallization), a suitable pH value resides around the isoelectric point (pH of 5.9) of L-Trp at which the solubility of L-Trp becomes low, namely a pH ranging from 4 to 7.

Such a mixing of the acidic (or alkaline) aqueous solution of L-Trp with the alkali (or acid) in order to maintain the pH of the solution to be crystallized (slurry to be crystallized) in the range of 3 to 8, preferably, in order to maintain a suitable pH value within this pH range, may be performed by gradually feeding the L-Trp solution and the neutralizing agent simultaneously by small portions to a crystallizer (referred to as simultaneous neutralization and crystallization).

In actually performing the simultaneous neutralization and crystallization, it is desired to initially prepare a slurry of seed crystals by adding the alkali (or acid) to a 1/5 to 1/20 volume portion of the acidic (or alkaline) aqueous solution of L-Trp, which is a stock solution for crystallization, for example, over 30 minutes. Of course, the flocculated L-Trp crystals of the present invention separately obtained may be used as the slurry of seed crystals.

Next, the remaining stock solution for crystallization and the neutralizing agent are simultaneously fed to the slurry of seed crystals in order to continuously neutralize the L-Trp containing pH solution and to achieve the crystallization of L-Trp. In this case, the neutralizing rate, which is the time period required for the simultaneous feeding of the stock solution for crystallization and the neutralizing agent, depends on the scale of crystallization. However, if the neutralizing rate is too fast, the process then comes close to the batch process for neutralization and crystallization, which is the one-way addition of the addition of the neutralizing agent to the whole volume of the L-Trp stock solution for crystallization or vice versa. Therefore, the addition of solution over a long period of time facilitates the flocculation of the crystals. When the scale is approximately $10^{-1}$ to $10^5$ liters, a time period of 1 to 4 hours is appropriate. No difference was noted in flocculation and crystallization within this range.

The higher temperature of crystallization, the more flocculation and crystallization are facilitated. However, decomposition of L-Trp is accelerated at high temperatures so that the temperature for crystallization is preferably between 20 and 50° C, most preferably between 30 and 40° C.

Where the concentration of L-Trp in the L-Trp stock solution for crystallization is as low as less than 30 g/l, the amount of L-Trp which remains in the mother liquor for the crystallization of L-Trp (solution obtained by removing the crystals from the slurry to be crystallized) increases. In this case, it is desired to previously increase the concentration of L-Trp in the stock solution for crystallization to 40 g/l or more. Where the pH of the liquid which flows through the decoloring resin is, e.g., about 2, and the concentration of L-Trp is sufficiently high, it is not necessary to increase the concentration of L-Trp. However, where the pH is 3 or more, the solubility of L-Trp around the neutral region is low s that the concentration of L-Trp cannot be increased and such is not preferred for neutralization and crystallization. It is thus undesired to use the solution which flows through the decoloring resin as the stock solution for crystallization as it is. It is desired to concentrate the solution prior to the treatment. In this case, concentration under reduced pressure using a concentrator can present difficulties because of foaming. In addition, energy costs are too much and such is not preferred. However, by adjusting the pH of the solution which passes through the decoloring resin to 2, passing the solution through a cationic exchange resin such as SK-1B (manufactured by Mitsubishi Chemical Industry Co., Ltd.), or the like to adsorb L-Trp onto the resin and then cyclizing an aqueous alkali solution of I N or more, preferably about 2 N, to a resin tower to elute L-Trp, an alkaline L-Trp elute of a high concentration can be obtained. The resulting L-Trp solution of high concentration is used as the stock solution for crystallization. Acid is added to the stock solution to simultaneously neutralize the solution and effect crystallization. By this procedure flocculated crystals of L-Trp can be crystallized at a high rate of recovery.

It has also found that in the simultaneous neutralization and crystallization of the present invention, when crystallization from the stock solution is performed in the presence of a readily water-soluble organic solvent, L-Trp crystals can be obtained with good selectivity and with reduced impurities such as pigments, and the like, i.e., higher purity, and the crystals separate well from the medium as do the crystals from the aqueous solution by simultaneous neutralization and crystallization. In order to provide an aqueous crystallization solution with a water-soluble organic solvent, an organic solvent such as 2-propanol, or the like may be added to the stock solution for crystallization in an amount of e.g., i0 to 30 v/v%, based on the stock solution for crystallization. The amount of the organic solvent added is chosen from the viewpoint of selectivity of pigment, economic considerations, safety, and the like.

Needless to say, it is preferred, in view of improving the rate of crystallizing L-Trp, to further cool the solution to be crystallized, after feeding the L-Trp aqueous solution (stock solution for crystallization) and the neutralizing agent to a crystallizer in order to achieve simultaneous neutralization and crystallization.

The L-Trp crystals precipitated from the solution to be crystallized can be isolated by any appropriate solid-liquid separation technique. Since the L-Trp crystals are flocculated crystals which exhibit good solid-liquid separation in a centrifuge, the crystals therefore can be efficiently isolated by centrifugation.

The method for crystallization of the present invention has been explained above with respect to L-Trp, but it is apparent that the method for crystallization can also be applied to D-Trp. An example of an aqueous solution of D-Trp which can be utilized in the method of the present invention is an aqueous solution obtained by a synthetic process for the production of D-Trp which is exemplified by a solution of D-tryptophan obtained by optical resolution of DL-aqueous and hydrolysis of the remaining D-acetyltryptophan.

Having generally described this invention, a further understanding can be obtained by reference to certain specific examples which are provided herein for purposes of illustration only and are not intended to be limiting unless otherwise specified.

EXAMPLE 1

(a) A L-Trp fermentation broth was obtained by the process described in Japanese Patent Application Laid-Open No. 61-199794. The cells were removed by precise filtration (MF). The concentration of L-Trp in the cell-free solution was 14 g/l.

After adjusting the pH of the solution to 3 with conc. sulfuric acid, 18.1 l of the cell-free solution was passed through a tower packed with 0.61 l of decoloring resin KS type manufactured by Hokuetsu Carbon at room temperature and SV =1. Next, by passing 11.0 l of water through the resin, L-Trp, which remained in the resin tower, was recovered. The concentration of L-Trp in the solution which passed through the decoloring resin was 7.5 g/l.

After adjusting the pH to 2 with conc. sulfuric acid, 29.1 l of the solution, which passed through the decoloring resin, was passed through a tower packed with 1.7 l of cation exchange resin (SK-IB; manufactured by Mitsubishi Chemical Industry Co., Ltd.) in order to adsorb L-Trp on the resin. After 2.4 l of 2N aqueous sodium hydroxide solution was cyclized and passed through the resin tower from the bottom, 1.9 l of water was further passed through the tower to elute L-Trp. The concentration and pH of L-Trp in the eluate were 49 g/l and 13.5, respectively.

While adjusting pH to the range of 6 to 7 with conc. sulfuric acid, a 250 ml portion of the cation exchange resin eluate wa charged into the crystallizer in order to precipitate the flocculated crystals of L-Trp, thereby forming a slurry of seed crystals (required time period, 20 minutes).

While stirring at 40° C, a 1.5 l portion of the remaining cation exchange resin eluate was added to the slurry over one hour. At the same time, conc. sulfuric acid was added at such a rate that the pH was maintained in the range of 6 to 7. Thus, neutralization and crystallization, i.e., simultaneous neutralization and crystallization, were performed. The solution to be crystallized was cooled to 30° C and allowed to stand at this temperature for 30 minutes.

The precipitated L-Trp crystals were centrifuged in a centrifuge (1700 g, 5 minutes). After the mother liquor was isolated, the crystals were washed with 140 ml of water to give 128 g of wet crystals.

The wet crystals were dried in a vacuum drying oven at 50° C. The weight was 60 g after the drying. The crystal habit of the dry crystals was still flocculated crystals. A microscopic photograph (40×) is shown in FIG. 1.

(b) The foregoing experiment was carried out without preparing the slurry of seed crystals. The time period required for the solution to crystallize to reach a state which is suitable for subjecting the solution to centrifugation (state that growth of crystals and new crystallization were not observed) was similar to that of Example 1. The resulting crystals were flocculated crystals similar to those shown in FIG. 1, in either the wet state or the dry state. In the crystallization operation which does not use a slurry of seed crystals, however, it was difficult to control pH.

COMPARATIVE EXAMPLE 1

The same cell-free solution of L-Trp, 1.0 l, as in Example 1 was contacted with a cationic exchange resin and then simultaneously neutralized and crystallized. The solution was centrifuged (1700 g, 15 minutes) in a manner similar to Example 1 (a) to give 28.8 g of wet crystals.

Figure 2:
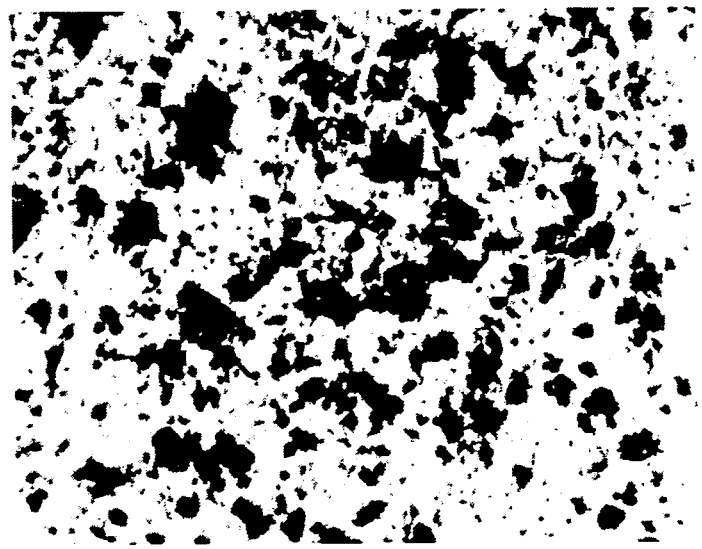
FIG. 2 is a microphotograph (40×) of the scaly microcrystals of L-Trp prepared by the process of Comparative Example 1.

The weight was 9.5 g after drying. The wet crystals and the dry crystals were both scaly micro-crystals. A microscopic photograph (40×) of the dry crystals is shown in FIG. 2.

The relationship between the quality of the crystals isolated in Example 1 (a) and Comparative Example 1 and the treatment with decoloring resin are shown in Table 1.

TABLE 1

|  | Example 1 | Comparative Example 1 |
| --- | --- | --- |
| Treatment with decoloring resin | positive | negative |
| Shape of crystals | flocculated crystals | scaly micro crystals |
| Time for centrifugation | 5 mins. | 15 mins. |
| Adhering moisture to the crystals prior to drying | 51% | 67% |
| L-Trp content in the crystals after drying | 99% | 93% |
| Transmittance of the crystals after drying (430 nm)*1 | 86% | 9% |

*1The measurement was made with a solution of 1.00 g of the dry crystals in 100 ml of water.

EXAMPLE 2

To 61 g of the L-Trp crystals obtained by the method described in Example 1 were added 635 ml of water and 10 ml of conc. sulfuric acid to prepare a solution (concentration of L-Trp: 67 g/l).

After 215 ml of 2-propanol/water (volume ratio, 1:1) was added to the solution, a 48% aqueous sodium hydroxide solution was added to a 62 ml portion of the mixture for simultaneous neutralization and crystallization, while adjusting the pH to 4. Thus, crystals of L-Trp were formed thereby preparing a slurry of seed crystals. Then, the remaining solution having been treated with resin and 48% aqueous sodium hydroxide solution were gradually added to the slurry at 35° C over an hour in order to keep the pH at 4 (simultaneous neutralization and crystallization).

After completion of the addition, the solution to be crystallized was cooled to 10° C and allowed to stand at this temperature for an hour. The crystals which precipitated were centrifuged to give 74 g of wet crystals. The wet crystals were flocculated crystals similar to those obtained in Example 1.

COMPARATIVE EXAMPLE 2

After 130 ml of 2-propanol/water (volume ratio, 1:1) was added to 610 ml of a solution of L-Trp crystals obtained in a manner similar to Example 2, 22 ml of 25% aqueous sodium hydroxide solution was added at one time (batch neutralization and crystallization). While keeping the pH at 4.1 and the temperature at 37° C, the mixture was stirred for an hour. The mixture was cooled to 10° C and allowed to stand for one more hour. Then the crystals were centrifuged to give 43 g of wet crystals. The wet crystals were scaly micro-crystals.

The relationship between the quality of the crystals isolated in Example 2 and in Comparative Example 2 and the treatment with decoloring resin is shown in Table 2.

TABLE 2

|  | Example 2 | Comparative Example 2 |
| --- | --- | --- |
| Method of crystallization | simultaneous neutralization and crystallization | batch neutralization and crystallization |
| Shape of crystals | flocculated crystal | scaly micro-crystal |
| Time for centrifugation | 5 mins. | 10 mins. |
| Adhesive moisture | 40% | 37% |

As described above the method of the present invention provides optically active tryptophan crystals which exhibit good solid-liquid separation, when isolated with a centrifuging machine. The crystals can be crystallized by simultaneous neutralization and crystallization, without adding any defoaming or crystallization catalyst or without heating at a high temperature.

Having now fully described the invention, it will be apparent to one of ordinary skill in the art that many changes and modifications can be made thereto without departing from the spirit or scope of the invention as set forth herein.

What is claimed as new and desired to be secured by Letters Patents of the U.S. is:

1. In a method for crystallizing optically active tryptophan through neutralization by mixing an acidic or alkaline aqueous solution of optically active tryptophan, which is obtained by the removal of impurities from an acidic or alkaline aqueous solution of optically active tryptophan containing impurities which inhibit flocculation and crystallization of optically active tryptophan, with an alkali or an acid, the improvement comprising: combining portions of an alkali or acid with portions of an acidic or alkaline aqueous solution of optically active tryptophan, from which the impurities have been removed, thereby neutralizing the aqueous solution containing optically active tryptophan such that the pH of the solution to be crystallized is kept in a range of 3 to 8, and simultaneously crystallizing optically active tryptophan as flocculated crystals.

2. The method of claim 1, wherein, in order to crystallize optically active tryptophan as flocculated crystals, said impurities are removed by passing said acidic or alkaline aqueous solution of optically active tryptophan containing the impurities through an adsorbent resin.

3. The method of claim 1 or 2, wherein, when the concentration of the optically active tryptophan in the aqueous solution to be neutralized is low, said aqueous tryptophan solution is made an aqueous alkaline solution of optically active tryptophan having a high concentration of not less than 50 g/l which is suitable for crystallization through neutralization, by previously passing said aqueous solution through a cationic exchange resin which adsorbs optically active tryptophan thereto and then eluting the optically active tryptophan with an alkali of a concentration of not less than 1 N.

4. The method of claim 3, wherein the concentration of optically active tryptophan in the aqueous solution to be neutralized is not greater than 30 g/l.

5. The method of claim 1, wherein an organic solvent easily miscible with water is present in said aqueous tryptophan containing solution from which optically active tryptophan is to be crystallized.

6. The method of claim 1, wherein the pH at which crystallization is effected is at about the isoelectric point of tryptophan.

7. The method of claim 1, wherein the portions of the alkali or acid and acidic or alkaline aqueous solution of optically active tryptophan are simultaneously added to a solution containing seed crystals of optically active tryptophan.

8. The method of claim 1, wherein the optically active tryptophan is neutralized and crystallized at a temperature of 20° C. to 50° C.

* * * * *

UNITED STATES PATENT AND TRADEMARK OFFICE
CERTIFICATE OF CORRECTION

PATENT NO. : 5,070,208
DATED : December 3, 1991
INVENTOR(S) : KENICHI YARITA ET AL It is certified that error appears in the above-identified patent and that said Letters Patent is hereby corrected as shown below:

Col.  Line 2,   16,  delete "18 g" and insert --1.8 g--;
3,   23,  delete "I" and insert --1--;
5,   28,  delete "s" and insert --so--;
5,   42,  delete "I" and insert --1--;
5,   64,  delete "i0" and insert --10--;
6,   21,  delete "DL-aqueous" and insert --DL-acetyltryptophan--;
6,   58,  delete "wa" and insert --was--;
8,   12.  delete "6I0" and insert --610--;
8,   16,  delete "4.I" and insert --4.1--.

Signed and Sealed this

Eighteenth Day of May, 1993

Attest:

MICHAEL K. KIRK

*Attesting Officer*      *Acting Commissioner of Patents and Trademarks*